(12) United States Patent
Hushon

(10) Patent No.: US 8,812,452 B1
(45) Date of Patent: Aug. 19, 2014

(54) CONTEXT-DRIVEN MODEL TRANSFORMATION FOR QUERY PROCESSING

(75) Inventor: John Daniel Hushon, Medfield, MA (US)

(73) Assignee: EMC Corporation, Hopkinton, MA (US)

( * ) Notice: Subject to any disclaimer, the term of this patent is extended or adjusted under 35 U.S.C. 154(b) by 604 days.

(21) Appl. No.: 12/495,215

(22) Filed: Jun. 30, 2009

(51) Int. Cl.
*G06F 7/00* (2006.01)
*G06F 17/00* (2006.01)

(52) U.S. Cl.
USPC .......................... 707/661; 707/666

(58) Field of Classification Search
USPC ........................ 707/739, 794, 705, 661, 666
See application file for complete search history.

(56) References Cited

U.S. PATENT DOCUMENTS

| | | | |
|---|---|---|---|
| 7,490,094 B2 * | 2/2009 | Bamba et al. .................. | 1/1 |
| 2004/0210552 A1 | 10/2004 | Friedman et al. | |
| 2007/0112718 A1 * | 5/2007 | Liu et al. ........................ | 706/47 |
| 2007/0185930 A1 * | 8/2007 | Betz et al. ...................... | 707/203 |
| 2008/0126397 A1 | 5/2008 | Alexander et al. | |
| 2008/0140786 A1 * | 6/2008 | Tran .............................. | 709/206 |
| 2008/0177622 A1 * | 7/2008 | Akkiraju et al. ............... | 705/10 |
| 2009/0012842 A1 * | 1/2009 | Srinivasan et al. ............. | 705/10 |
| 2010/0268644 A1 * | 10/2010 | Sobel et al. .................... | 705/44 |

OTHER PUBLICATIONS

S. Decker et al., "Triple—an RDF Rule Language with Context and Use Cases," W3C Workshop on Rule Languages for Interoperability, Apr. 27-28, 2005, 6 pages, Washington, D.C., USA.
A. Billig et al., "Platform Independent Model Transformation Based on Triple," Lecture Notes in Computer Science, 2004, 20 pages, vol. 3231.
O. Corby et al., "A Conceptual Graph Model for W3C Resource Description Framework," Proceedings of the 8th International Conference on Conceptual Structures (ICCS), 2000, 14 pages.

* cited by examiner

*Primary Examiner* — Hosain Alam
*Assistant Examiner* — Navneet K Ahluwalia
(74) *Attorney, Agent, or Firm* — Ryan, Mason & Lewis, LLP (57) ABSTRACT

In an information management system, multiple models are utilized to characterize stored information. A query directed to the stored information is received, and at least one contextual indicator is extracted, inferred or otherwise determined from the received query. The contextual indicator determined from the received query is applied to a meta-model that includes linkages between attributes of respective ones of the multiple models, where each of the linkages comprises one or more associated contextual properties, in order to generate a transformed meta-model specifying an authoritative policy result for processing the query responsive to the contextual indicator. The query is then processed in accordance with the authoritative policy result specified in the transformed meta-model.

21 Claims, 4 Drawing Sheets

CONTEXT-DRIVEN MODEL TRANSFORMATION FOR QUERY PROCESSING

FIELD OF THE INVENTION

The present invention relates generally to the field of information management, and more particularly to techniques for processing queries in an information management system.

BACKGROUND OF THE INVENTION

Information management systems often utilize models to characterize managed information in order to facilitate the processing of queries directed to that information. The complexity of such models generally depends on the type of system, and the complexity compounds as multiple independent systems leverage their own instances of this information, usually in a different modeled form. For example, single-model, single-entity (SMSE) systems are readily characterizable by a particular model, consistent among participating systems, specifically for the use in managing a given entity. In systems of this type, issues such as upgrades, backward compatibility, forward integration, information contracts, access control, and compliance can be addressed in a straightforward manner using conventional techniques across a multitude of system boundaries.

Additional complexity is introduced in multi-model, single-entity (MMSE) systems, which typically need to incorporate functionality for transforming from one modeled foam to another. For example, the models may differ in terms of the manner in which particular attributes are represented or linked. Issues such as those identified above that are straightforward to deal with in SMSE systems can cause the number of model versions required in an MMSE system to increase exponentially. This can have a negative impact on query processing efficiency and system throughput performance.

Such problems are magnified in multi-model, multi-entity (MMME) systems, in which hierarchical entity domains bring another exponential increase in complexity. The hierarchical relationships in such systems introduce additional issues such as directional navigability and multiple inheritance.

There are a number of known approaches to model version complexity reduction, typically involving version control strategies. For example, these strategies may include backward compatibility limitations as well as attribute decomposition to reduce variance between models. However, such complexity reduction techniques do not adequately address the substantial increase in complexity associated with MMSE and MMME systems.

In information management systems involving semantically modeled data, the above-noted models may make use of the Resource Description Framework (RDF) of the World Wide Web Consortium (W3C). RDF is a language for representing information about resources in the web. It identifies such resources using Uniform Resource Identifiers (URIs) and models statements about the resources as a directed graph. A given such statement is represented by the elements (Subject, Predicate, Object), also referred to as an RDF triple.

Additional details regarding RDF are described in the following W3C Recommendations, all dated Feb. 10, 2004 and incorporated by reference herein: RDF/XML Syntax Specification (Revised); RDF Vocabulary Description Language 1.0: RDF Schema; RDF: Concepts and Abstract Syntax; RDF Semantics; and RDF Test Cases. See also W3C Recommendation RDFa in XHTML: Syntax and Processing, Oct. 14, 2008, which is also incorporated by reference herein.

It is also known to incorporate context information into models based on RDF. See, for example, S. Decker et al., "TRIPLE—an RDF Rule Language with Context and Use Cases," W3C Workshop on Rule Languages for Interoperability, 27-28 Apr. 2005, Washington, D.C., USA; and A. Billig et al., "Platform Independent Model Transformation Based on Triple," Lecture Notes in Computer Science, Vol. 3231, pp. 493-511, 2004.

However, these techniques fail to provide a scalable approach that is suitable for significantly reducing model version complexity, particularly in MMSE and MMME information management systems.

SUMMARY OF THE INVENTION

Illustrative embodiments of the present invention overcome the above-described deficiencies of conventional practice by providing context-driven model transformation to facilitate query processing in an information management system. This transformation in one or more of the illustrative embodiments is based on establishing context-based linkages between predicates of RDF statements supported across multiple independent but linkable entity namespaces.

In one aspect of the invention, an information management system utilizes multiple models to characterize stored information. A query directed to the stored information is received, and at least one contextual indicator is determined from the received query. For example, the contextual indicator may be extracted from the query, inferred from the query based on associated meta-information such as an authorization token, or determined using other techniques. The contextual indicator extracted, inferred or otherwise determined from the received query is applied to a meta-model that includes linkages between attributes of respective ones of the multiple models, where each of the linkages comprises one or more associated contextual properties, in order to generate a transformed meta-model specifying an authoritative policy result for processing the query responsive to the determined contextual indicator. The query is then processed in accordance with the authoritative policy result specified in the transformed meta-model.

The illustrative embodiments advantageously overcome the above-noted drawbacks of conventional approaches to the use of context information in query processing. For example, the context-driven model transformation approach of the illustrative embodiments provides improved processing of a wide variety of types of queries, thereby improving system efficiency, accuracy and throughput, particularly in MMSE and MMME systems.

These and other features and advantages of the present invention will become more readily apparent from the accompanying drawings and the following detailed description.

DETAILED DESCRIPTION

The present invention will be described herein with reference to exemplary information management systems and associated query sources, information managers, servers and other processing devices. It is to be appreciated, however, that the invention is not restricted to use with the particular illustrative system and device configurations shown.

Figure 1:
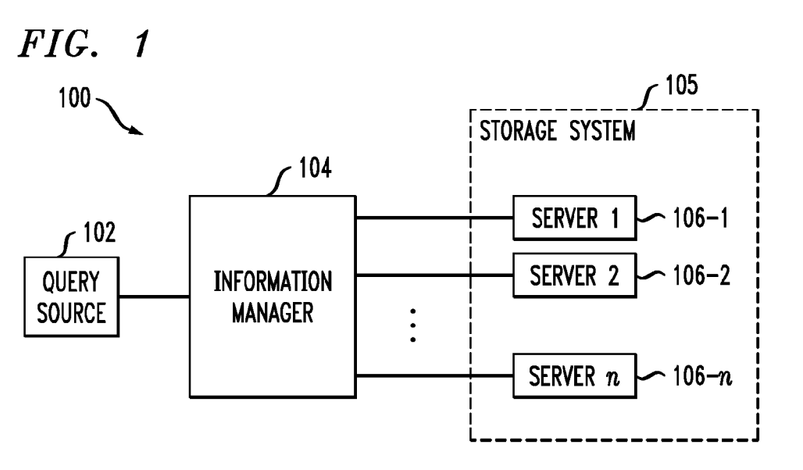
FIG. 1 is a block diagram showing one example of an information management system in an illustrative embodiment of the invention.

FIG. 1 shows an example of an information management system 100 which includes a query source 102, an information manager 104, and a storage system 105 comprising servers 106-1, 106-2, . . . 106-*n*. The system 100 is configured to process queries using a context-driven model transformation approach to be described in greater detail below.

The query source 102 may comprise a client device such as a computer, a mobile telephone, a personal digital assistant (PDA), a wireless email device, a workstation, a kiosk, a television set-top box, a game console, or more generally any type of information processing device from which a user or other client may wish to generate queries for information stored on one or more of the servers 106.

In other embodiments, at least a portion of the query source 102 may be internal to the information manager 104. For example, the information manager may be configured to generate prototype queries so as to verify reachability of certain stored information by particular entities in designated contexts. Thus, information manager 104 may process externally-generated or internally-generated queries, in any combination.

The query source 102 will generally include a user interface through which an associated user can interact with the information management system 100. This interaction allows the user to generate queries for information stored on the servers 106, and to receive such information from the servers via the information manager 104. Also, the query source 102 and the information manager 104 may be combined into a single device. Thus, the information manager may be configured to include the above-noted user interface, such that a user can interact directly with the information manager.

The information manager 104 is an example of what is more generally referred to herein as a "processing device." Such a device generally comprises at least one processor and an associated memory, and implements functional modules for processing queries in a manner to be described herein.

The storage system 105 may comprise, for example, a single-site storage system, or a distributed storage system in which the servers 106 need not be located at a single site but are accessible via a network such as the Internet. The latter type of arrangement may be implemented as a so-called "cloud" storage system. A particular server 106 may thus be implemented as a computer or other stand-alone processing platform, or may be distributed over multiple processing platforms each comprising one or more separate computers. The servers may be part of a single storage service or various subsets thereof may each be associated with independent storage services. The storage system may thus comprise multiple federated storage systems, with each server potentially indicating a different federated storage system. Numerous other arrangements of multiple servers are possible in the storage system 105. These servers can communicate with other elements of the information management system 100 over any type of network, such as a wide area network (WAN), a local area network (LAN), a satellite network, a telephone or cable network, or various portions or combinations of these and other types of networks.

It is to be appreciated that a given embodiment of the system 100 may include multiple instances of query source 102, information manager 104 and storage system 105, although only single instances of such components are shown in the simplified system diagram for clarity of illustration. For example, a given user may have multiple personal computing devices that access different sets of servers over different networks via different information managers. The particular number of servers in a given such set of servers is arbitrary and may vary depending upon the application.

Figure 2:
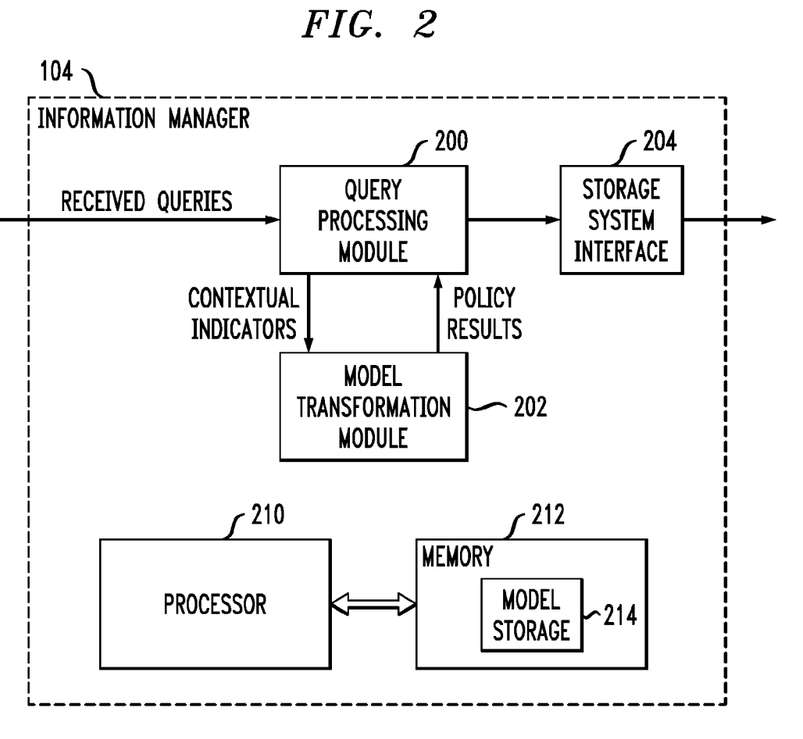
FIG. 2 is a more detailed view of an information manager of the FIG. 1 system.

FIG. 2 shows a more detailed view of the information manager 104 in an illustrative embodiment. The information manager in this embodiment comprises a query processing module 200 coupled to a model transformation module 202. The query processing module 200 receives queries from query source 102, determines contextual indicators from those queries, and supplies those contextual indicators to the model transformation module 202. The model transformation module 202 returns an authoritative policy result to the query processing module for each query based on its associated contextual indicator. The query processing module 200 then interacts with the storage system 105 via interface 204 in a manner consistent with the authoritative policies returned by the model transformation module. The interface 204 may comprise a network interface including conventional transceiver circuitry of a type well known to those skilled in the art.

The information manager 104 in this embodiment further comprises a processor 210 coupled to a memory 212. The processor 210 may comprise a microprocessor, a microcontroller, an application-specific integrated circuit (ASIC), a field programmable gate array (FPGA) or other type of processing circuitry, as well as portions or combinations of such circuitry elements.

The modules 200 and 202 of the information manager 104 may be implemented in whole or in part in the form of one or more software programs stored in memory 212 and executed by processor 210. The memory 212 may be viewed as an example of what is more generally referred to herein as a "computer program product" having executable computer program code embodied therein. Such memories may comprise electronic memories such as random access memory (RAM), read-only memory (ROM) or other types of memory, in any combination. The computer program code when executed in a processing device such as information manager 104 causes the device to perform corresponding operations associated with functions such as query processing and model transformation. One skilled in the art would be readily able to implement such software given the teachings provided herein. Other examples of computer program products embodying aspects of the invention may include, for example, optical or magnetic disks.

The memory 212 further comprises a model storage element 214 for storing one or more meta-models each comprising contextual linkages between multiple independent models characterizing information stored in the storage system 105. Element 214 may be implemented as a meta-structural registry or other type of repository. In other embodiments, the meta-models may be stored externally to the information manager 104 and accessed as needed. Such an external storage arrangement may involve mapping retrieved models into a particular format, such as RDF.

Figure 3:
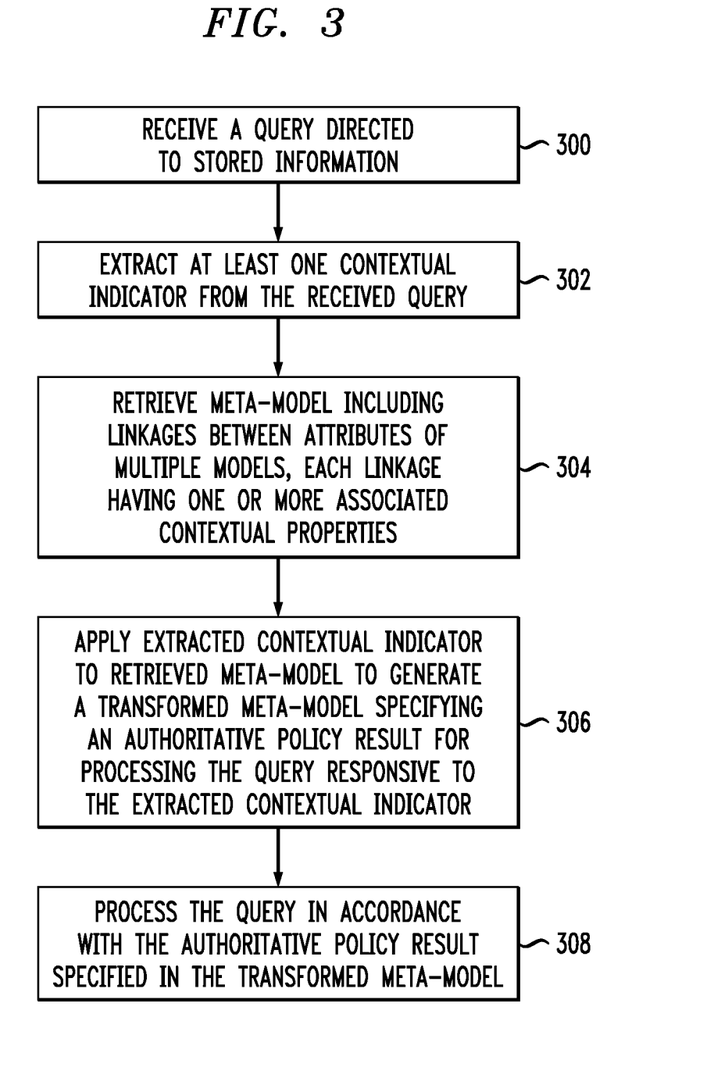
FIG. 3 is a flow diagram of an exemplary technique for query processing based on context-driven model transformation in the system of FIG. 1.

Referring now to FIG. 3, a flow diagram illustrating the processing of a given query by the information manager 104 is shown. This context-driven model transformation approach includes steps 300 through 308.

In step 300, a query is received in the information manager 104 from the query source 102. The query is directed to information stored in one or more of the servers 106 of the storage system 105.

In step 302, at least one contextual indicator is extracted from the query in the query processing module 200. This extraction may be based on semantic processing of the query using known context recognition techniques, and the resulting indicator is supplied by the query processing module to the model transformation module 202. The contextual indicator need not take any particular form. For example, context can also be associated with a query by a participating service using application logic of the service. This may involve a declared annotation on a deployment descriptor (e.g., I'm using the v1.1 Entity X model, or my role is a customer).

Although in this embodiment the contextual indicator is extracted from the query, other embodiments may utilize different techniques to determine the contextual indicator from the query. For example, the contextual indicator may be inferred from the query based on associated meta-information such as an authorization token. It is also possible to determine an applied context derived from the structure of an event associated with the query. Context inferring or deriving arrangements of this type may be particularly useful in situations in which it is not possible to directly amend a query to incorporate one or more contextual indicators. The above meta-information may be associated with a query through a mediator, or directly sourced from an external context processor that can translate session or connection oriented meta-information to a specific context of use.

In step 304, the model transformation module 202 retrieves a meta-model from model storage 214 of memory 212. The meta-model includes linkages between attributes of multiple independent models each characterizing portions of the information stored in the storage system 105. Moreover, each of at least a subset of these linkages comprises one or more associated contextual properties. The contextual properties generally characterize the impact of particular types of context on the corresponding linkages. For example, the information management system 100 may comprise a MMME system in which each of a plurality of entities has a different associated policy for utilization of the stored information. The entities may be arranged in the form of a directed graph with the meta-model characterizing contextual relationships between the entities. A given one of the linkages in the meta-model may have a plurality of properties each associated with a different contextual indicator, with each such property being associated with a different policy for processing a query.

In step 306, the extracted contextual indicator is applied to the retrieved meta-model in order to generate a transformed meta-model specifying an authoritative policy result for processing the query responsive to the extracted contextual indicator.

In step 308, the query is processed in accordance with the authoritative policy result specified in the transformed meta-model.

As indicated above, the query processed in the flow diagram of FIG. 3 may comprise a query generated internally to the information manager 104. For example, it may comprise a prototype query generated for a given set of policies against a plurality of classes of the meta-model, with the query being processed to determine portions of the stored information that are reachable by a particular entity.

The independent models that are characterized by the meta-model retrieved in step 304 may be in a particular defined format, such as RDF. In such an embodiment, one or more of the linkages of the meta-model may comprise linked RDF triples. For example, the meta-model may be configured such that a predicate of a given RDF triple is subject to different interpretations for different contextual indicators. The transformed meta-model in this case may specify a particular one of the interpretations for the predicate of the given RDF triple in accordance with the value of the extracted, inferred or otherwise determined contextual indicator.

The different contextual indicators in a given embodiment may be derived from independent graphs having respective differentiated namespaces. The differentiated namespaces may be determined by a uniqueness function established on import of the associated information to the system in order to maintain future model independence by supporting divergence of namespaces over time.

More particular examples of differentiated namespaces for a medical information management application will be described below in conjunction with FIGS. 4 and 5. A corresponding fused meta-model is shown in FIG. 6.

Figure 4:
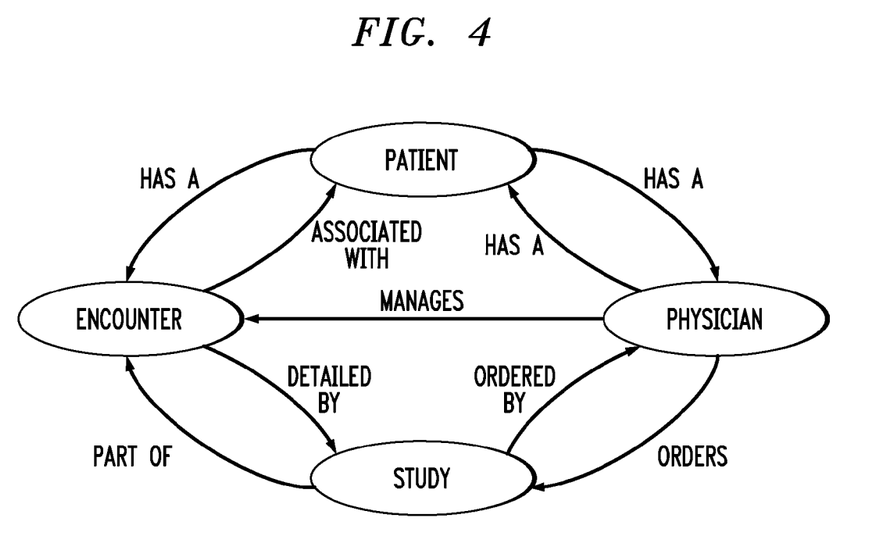
FIGS. 4 and 5 illustrate exemplary models for respective independent namespaces in a medical information management application.

Referring initially to FIG. 4, a model is shown providing an ontology for a clinical namespace of the medical information management application. This ontology comprises a graph having nodes given by Patient, Physician, Encounter and Study. The links specify the relationships between the nodes. More specifically, Patient has Encounter, and Encounter is associated with Patient; Physician has Patient, and Patient has Physician; Physician orders Study, and Study is ordered by Physician; Encounter is detailed by Study, and Study is part of Encounter.

Figure 5:
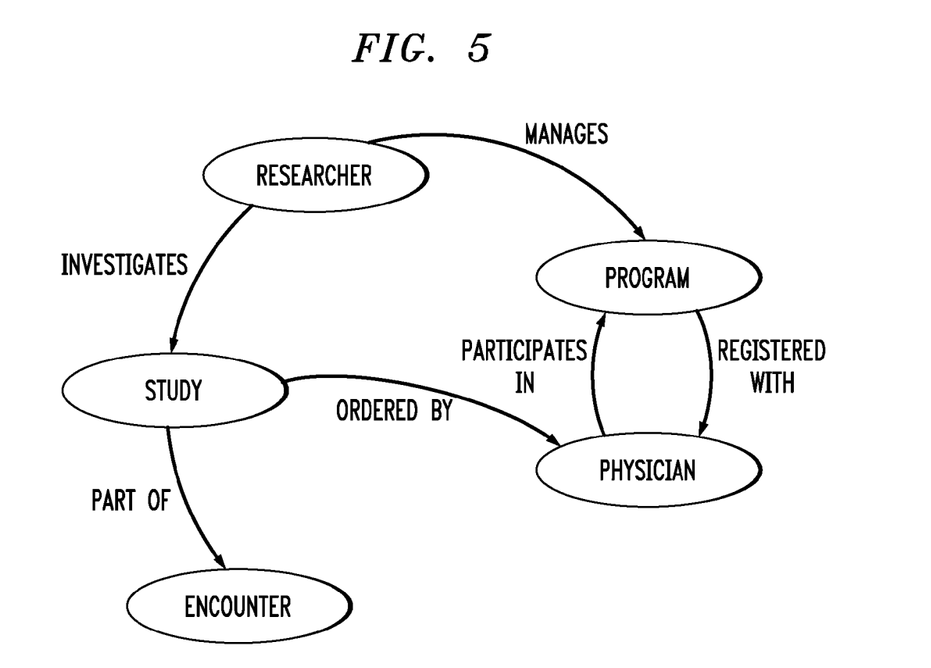

An independent model providing an ontology for a research namespace is shown in FIG. 5. This ontology comprises a graph having nodes given by Researcher, Program, Physician, Encounter and Study. The links again specify the relationships between the nodes. More specifically, Researcher investigates Study and manages Program; Physician participates in Program, and Program is registered with Physician; Study is ordered by Physician; and Study is part of Encounter.

Figure 6:
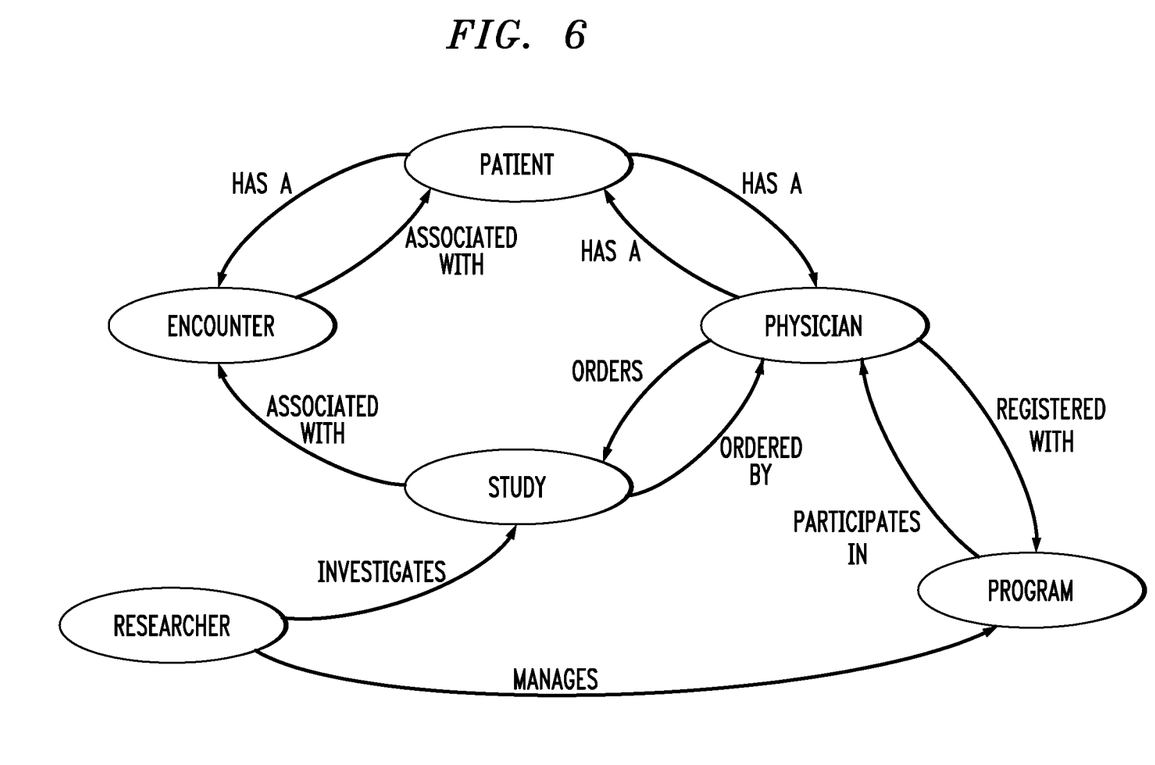
FIG. 6 shows a meta-model that may include context-based linkages between attributes of the models of FIGS. 4 and 5.

FIG. 6 shows the fused meta-model combining the independent namespace ontologies of FIGS. 4 and 5.

The manner in which the meta-model of FIG. 6 can incorporate linkages with contextual properties will now be described.

Assume that it is desirable to assert privacy policies on certain model linkages involving a particular patient denoted Patient 1. This can be accomplished by associating contextual properties with linkages that define relationships among the nodes of the meta-model. For example, the patient may have had multiple encounters and may want to adopt different clinical policies defining different levels of researcher access for the various encounters. In this case, a given base RDF triple may be modified as follows to incorporate the desired contextual properties:

[Patient 1 in context of Encounter A] governed by [Clinical Policy X]
[Patient 1 in context of Encounter B] governed by [Clinical Policy Y]
[Patient 1 in context of Encounter C] governed by [Clinical Policy Z]

where A, B and C denote different encounters, and X, Y and Z denote different clinical policies to be applied to the respective encounters. The above modified RDF triples may be further augmented with additional modified RDF triples as follows:

[Patient 1 in context of Encounter A] governed by [Research Policy J]

[Patient 1 in context of Encounter B] governed by [Research Policy K]
[Patient 1 in context of Encounter C] governed by [Research Policy L]
where J, K and L denote different classes or instances of research policy. The specified research policy may, for example, enable or block query-based access to the various encounters associated with this particular patient. This approach could be further extended to automate the application of policy to any direct or indirect links between any two nodes in the meta-model. For example, the following modified RDF triples:
[Patient 1 in context of Study D] governed by [Research Policy M]
[Patient 1 in context of Study E] governed by [Research Policy N]
[Patient 1 in context of Study F] governed by [Research Policy O]
can be used to determine an appropriate research policy to be applied in the context of a particular identified study via the indirect linkage between the Patient and Study nodes in the meta-model.

It should be noted that the particular RDF triple formats shown above are presented by way of illustrative example only, and numerous alternative formats may be used in implementing the invention.

The particular medical information management application described in conjunction with FIGS. 4, 5 and 6 is just an example of one use case, and numerous other use cases are possible.

As another example use case, consider a business unit including a parent company and a number of partner companies. The information management application in this case is the sharing of customer data between the parent company and its partners. Predicate logic, potentially derived from structured model annotations, provides the business unit with the ability to associate policies, such as visibility (e.g., suppression or redaction), mutability, audit log requirements, and resource state associative groupings, with particular contextual properties of linkages in a meta-model. The business unit can thus facilitate the sharing of customer data using a derivative mapping formed as a meta-structure which overlies a multitude of separate federate ontologies. The corresponding meta-model can be used to rationalize across the federate ontologies, and can be used to describe the relationships between the federates, as well as the associated policies. These associated policies, as represented as properties of the parent model, can now be rationalized across both the parent namespace as well as across the partner namespaces. Properties such as reflexive, inreflexive, transitive, asymmetric and others impart directionality to denote their relationship to similar properties within the federated entity namespace properties. For example, enterprise policies for social security number sharing can be enforced to ensure that even if one federate may allow the export of a social security number, it will not be available to other federates.

In an arrangement of this type, links (e.g., statements) between federates may be made dependent on the context of use (e.g., multiplicity of associations) by establishing contextual properties associated with a link that derives from a consistent class (e.g., formal subclass). It can be differentiated in such a way that context-driven navigation will resolve the appropriate contextual relationships and associations so as to impart appropriate controls. The controls elaborated by the contextual relationships and associations can be further extended to elaborate their own policies. Class-based query mechanisms may be used to ensure that for a given processed query, there will be a directed graph of results in which the ordering of results will be significant. For example, the ordering when applied against a top level graph (e.g., the ontology built across the shared namespaces) will provide a singular authoritative policy result for a given query context.

Embodiments of the invention can be used to leverage a contextual query against a semantic store in order to resolve a mapping from a canonical model into a contextual target model. Examples of suitable contextual properties in the MMME domain include directionality of linkage, validity of relationships, visibility limits, relative ordering semantics, and versioning of models, mappings, transforms and linkages. The semantic store can utilize contextually tagged links between entities in order to resolve a result set that represents a target model. More specifically, the store could utilize entity linked transformational structures that are appropriately contextually tagged and ordered so as to produce a source to target model transformation. The target model can be leveraged to construct a dynamic itinerary, which may then be executed by services which would perform processing steps such as extract, transform and load in a prescribed order to service a contextual event.

A given embodiment may thus provide "schemaless" RDF triple stores and linkages between objects that are described by flexible context predicates. Such an arrangement provides the ability to establish classes of contextual linkages that through semantic expression allow for the query of resources based upon these predicates. The assembly of a graph based upon these objects can be expressed based upon a vertex, into a navigable structure which represents the target model. Subsequent queries across the entities that make up the result set can be used for link minimization, attachment of linkage driven transforms, and navigation through a dicyclic graph to present ordering information critical to information orchestration. The resultant transformed model could be used to drive an itinerary.

Additional features that may be implemented in a given embodiment of the invention include contextual namespace enhancement of RDF Subject, Predicate and Object elements, support for runtime namespace rationalization as a set of directed associations in order to construct "operational ordering" behaviors (e.g., who has the ability to override whom), extension of namespace rationalization with applicable contexts as properties on the namespace directed relationships that can be used to ensure a singular resolution of a multitude of associated policies, and support for validation queries to ensure monotonicity of policies for a given context (e.g., one and only one authoritative response for a contextual policy query). Although a given query might otherwise result in the delivery of a number of potential policies in effect, the context-driven meta-model transformation can ensure that one and only one policy will be delivered as the authoritative policy.

The illustrative embodiments described herein provide a number of significant advantages over conventional techniques for query processing in an information management system. For example, query processing is made more accurate and efficient by use of meta-models incorporating context information in the manner described herein, thereby facilitating the implementation of MMSE and MMME systems.

As indicated above, the query processing functionality can be implemented at least in part in the form of one or more software programs stored in memory and executed by a processor of a processing device such as a client device, controller or server. A memory having such program code embodied therein is an example of what is more generally referred to herein as a "computer program product."

It should again be emphasized that the above-described embodiments of the invention are presented for purposes of illustration only. Many variations and other alternative embodiments may be used. For example, although described in the context of particular system and device configurations, the techniques are applicable to a wide variety of other types of information management systems and processing devices. The particular process steps used to transform a model based on extracted, inferred or otherwise determined contextual indicators, and to process associated queries responsive to such indicators, may be varied in alternative embodiments. In addition, any simplifying assumptions made above in the course of describing the illustrative embodiments should also be viewed as exemplary rather than as requirements or limitations of the invention. Numerous other alternative embodiments within the scope of the appended claims will be readily apparent to those skilled in the art.

What is claimed is:

1. A method for use in an information management system in which multiple models are utilized to characterize stored information, the method comprising the steps of:

receiving a query directed to the stored information;

determining at least one contextual indicator from the query;

applying said at least one contextual indicator to a meta-model including a plurality of linkages between attributes of respective ones of the multiple models, each of said linkages comprising one or more associated contextual properties, to generate a transformed meta-model specifying an authoritative policy result for processing the query responsive to said at least one contextual indicator; and processing the query in accordance with the authoritative policy result specified in the transformed meta-model for the at least one contextual indicator;

wherein different contextual indicators are associated with different transformed meta-models which specify different authoritative policy results to be applied when processing a given query;

wherein a given one of the plurality of linkages of the meta-model has two or more policies associated therewith and the transformed meta-model specifies a given one of the two or more policies as the authoritative policy result; and wherein the steps are performed at least in part by a processing device comprising a processor coupled to a memory.

2. The method of claim 1 wherein the information management system comprises a MMME system in which each of a plurality of entities has a different associated policy for utilization of the stored information.

3. The method of claim 2 wherein the entities are arranged in the form of a directed graph and the meta-model characterizes contextual relationships between the entities.

4. The method of claim 1 wherein a given one of the linkages in the meta-model has a plurality of properties each associated with a different contextual indicator.

5. The method of claim 4 wherein each such property can be associated with a different policy for processing a query.

6. The method of 1 wherein the query comprises a prototype query generated for a given set of policies against a plurality of classes of the meta-model and the query is processed to determine portions of the stored information that are reachable by a particular entity.

7. The method of claim 1 wherein at least a portion of the stored information is characterized by one or more RDF models.

8. The method of claim 7 wherein one or more of the linkages of the meta-model comprise linked RDF triples.

9. The method of claim 7 wherein the meta-model is configured such that a predicate of a given RDF triple is subject to different interpretations for different contextual indicators.

10. The method of claim 9 wherein the different contextual indicators are derived from independent graphs having respective differentiated namespaces.

11. The method of claim 10 wherein at least one of said differentiated namespaces is determined by a uniqueness function established on import in order to maintain future model independence by supporting divergence of namespaces over time.

12. The method of claim 9 wherein the transformed meta-model specifies a particular one of the interpretations for the predicate of the given RDF triple in accordance with the value of the contextual indicator.

13. The method of claim 1 wherein the meta-model provides namespace rationalization as a set of directed associations in order to construct operational ordering behaviors.

14. The method of claim 1 wherein the meta-model further provides extension of namespace rationalization with applicable contexts as properties on namespace directed relationships to ensure a singular resolution of multiple associated policies responsive to the query.

15. A computer program product comprising a non-transitory processor-readable storage medium having encoded therein executable code of one or more software programs, wherein the one or more software programs when executed by a processor implement the steps of the method of claim 1.

16. An apparatus comprising:

a processing device having a processor coupled to a memory and configured for implementation in an information management system in which multiple models are utilized to characterize stored information;

wherein the processing device further comprises:

a query processing module configured to receive a query directed to the stored information and to determine at least one contextual indicator from the query; and a model transformation module configured to apply said at least one contextual indicator to a meta-model including a plurality of linkages between attributes of respective ones of the multiple models, each of said linkages comprising one or more associated contextual properties, and to generate a transformed meta-model specifying an authoritative policy result for processing the query responsive to said at least one contextual indicator;

wherein the query is processed by the query processing module in accordance with the authoritative policy result specified in the transformed meta-model for the at least one contextual indicator;

wherein different contextual indicators are associated with different transformed meta-models which specify different authoritative policy results to be applied when processing a given query; and wherein a given one of the plurality of linkages of the meta-model has two or more policies associated therewith and the transformed meta-model specifies a given one of the two or more policies as the authoritative policy result.

17. The apparatus of claim 16 wherein the processing device comprises an information manager configured for communication with one or more servers of the information management system.

18. The apparatus of claim 16 wherein the server implements an RDF processing engine associated with an RDF model characterizing at least a portion of the stored information.

19. An information management system comprising:

a plurality of servers for storing information characterized by a plurality of models; and at least one processing device configured to communicate with the plurality of servers;

wherein the processing device comprises:

a query processing module configured to receive a query directed to the stored information, and to determine at least one contextual indicator from the query; and a model transformation module configured to apply said at least one contextual indicator to a meta-model including a plurality of linkages between attributes of respective ones of the multiple models, each of said linkages comprising one or more associated contextual properties, and to generate a transformed meta-model specifying an authoritative policy result for processing the query responsive to said at least one contextual indicator;

wherein the query is further processed by the query processing module in accordance with the authoritative policy result specified in the transformed meta-model for the at least one contextual indicator;

wherein different contextual indicators are associated with different transformed meta-models which specify different authoritative policy results to be applied when processing a given query; and wherein a given one of the plurality of linkages of the meta-model has two or more policies associated therewith and the transformed meta-model specifies a given one of the two or more policies as the authoritative policy result.

20. The system of claim 19 wherein the processing device comprises an information manager coupled between the plurality of servers and a client device from which the query is received over a network.

21. The method of claim 1 wherein the transformed meta-model generated in the applying step specifies at least another authoritative policy result for processing the query for at least another contextual indicator.

* * * * *

UNITED STATES PATENT AND TRADEMARK OFFICE
CERTIFICATE OF CORRECTION

PATENT NO.        : 8,812,452 B1
APPLICATION NO.   : 12/495215
DATED             : August 19, 2014
INVENTOR(S)       : John Daniel Hushon

Page 1 of 1

It is certified that error appears in the above-identified patent and that said Letters Patent is hereby corrected as shown below:

In the Specification,

Column 1, line 32, please change "foam" to --form--

Signed and Sealed this
Sixth Day of January, 2015

Michelle K. Lee
*Deputy Director of the United States Patent and Trademark Office*